US012055611B2

(12) United States Patent
Biber

(10) Patent No.: US 12,055,611 B2
(45) Date of Patent: Aug. 6, 2024

(54) APPARATUS AND METHOD FOR SUPPORTING A SHIMMING OF A MAGNETIC RESONANCE APPARATUS

(71) Applicant: Siemens Healthcare GmbH, Erlangen (DE)

(72) Inventor: Stephan Biber, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 7 days.

(21) Appl. No.: 17/705,671

(22) Filed: Mar. 28, 2022

(65) Prior Publication Data

US 2022/0308140 A1 Sep. 29, 2022

(30) Foreign Application Priority Data

Mar. 29, 2021 (DE) ...................... 10 2021 203 139.0

(51) Int. Cl.
*G01R 33/3875* (2006.01)
*G01R 33/3873* (2006.01)
*A61B 5/00* (2006.01)
*A61B 5/055* (2006.01)

(52) U.S. Cl.
CPC ..... *G01R 33/3875* (2013.01); *G01R 33/3873* (2013.01); *A61B 5/0046* (2013.01); *A61B 5/055* (2013.01)

(58) Field of Classification Search
CPC ............ G01R 33/3875; G01R 33/3873; A61B 5/0046; A61B 5/055
See application file for complete search history.

(56) References Cited

U.S. PATENT DOCUMENTS

| 5,744,960 A * | 4/1998 | Pulyer ................ G01R 33/3808 324/319 |
| 7,196,520 B2 | 3/2007 | Shen et al. |
| 2013/0235969 A1* | 9/2013 | Winter ................. A61N 5/1079 378/4 |
| 2014/0180059 A1* | 6/2014 | Winter ................. A61N 5/1001 600/411 |
| 2018/0224512 A1* | 8/2018 | Poole ..................... G01R 33/36 |
| 2018/0238978 A1* | 8/2018 | McNulty .............. G01R 33/365 |

FOREIGN PATENT DOCUMENTS

| DE | 19923947 A1 | 12/2000 |
| DE | 102008009674 A1 | 8/2009 |

* cited by examiner

*Primary Examiner* — Dixomara Vargas
(74) *Attorney, Agent, or Firm* — Banner & Witcoff Ltd.

(57) ABSTRACT

A magnetic resonance apparatus may include at least one sensor and a controller. The magnetic resonance apparatus is positionable in an examination room. A spatial location of the magnetic resonance apparatus in the examination room can be determined using the sensor. In a method for supporting an adjustment of a shim parameter of a magnetic resonance apparatus, a current spatial location of the magnetic resonance apparatus in an examination room is determined using the sensor, and a shim parameter of at least one shim element of the magnetic resonance apparatus is determined based on the current spatial location of the magnetic resonance apparatus and information of a magnetic field database. The magnetic field database may include information about a spatial location of the magnetic resonance apparatus and also magnetic field data correlated with the spatial location.

15 Claims, 4 Drawing Sheets

APPARATUS AND METHOD FOR SUPPORTING A SHIMMING OF A MAGNETIC RESONANCE APPARATUS

CROSS REFERENCE TO RELATED APPLICATIONS

This patent application claims priority to German Patent Application No. 10 2021 203 139.0, filed Mar. 29, 2021, which is incorporated herein by reference in its entirety.

BACKGROUND

Field

The disclosure relates to a magnetic resonance apparatus, comprising at least one sensor, wherein the magnetic resonance apparatus is able to be positioned in an examination room and wherein the at least one sensor is embodied to determine a spatial location of the magnetic resonance apparatus in the examination room. The disclosure further relates to a method for supporting an adjustment of a shim parameter of a magnetic resonance apparatus.

Related Art

The presence of a magnetic field that is as homogeneous as possible represents a basic requirement for many magnetic resonance apparatuses. Inhomogeneities of the magnetic field can stem in such cases from a magnet of the magnetic resonance apparatus, but also from external influences such as e.g. (electro) magnetic fields and/or scattered electromagnetic radiation from the environment. Construction materials of a building in which the magnetic resonance apparatus is accommodated can also represent an external influence that has a negative effect on a homogeneity of the magnetic field of the magnetic resonance apparatus. For insuring high-quality imaging an adjustment of the magnetic field is typically required with magnetic resonance apparatuses. For such an adjustment, various methods also known as "shimming" are used. In such methods shim elements, such as for example small iron plates and/or electronic shim coils, are used in order to obtain a main magnetic field that is as homogeneous as possible.

For example, a main magnetic field of the magnetic resonance apparatus is able to be compensated for linearly in three spatial directions by an adjustment of currents by gradient coils of the magnetic resonance apparatus. It is however likewise possible to use separate shim coils in order to compensate for higher-order inhomogeneities. On the other hand, small iron plates are usually mounted at prespecified positions on the magnetic resonance apparatus. By selecting a number of the small iron plates, a position of the small iron plates and/or an orientation of the small iron plates the magnetic field is basically able to be set very exactly. The setting of the magnetic field by means of the installation of small iron plates represents a known service method, which is typically carried out during an initial installation of the magnetic resonance system.

The known shimming methods are based on the magnet of the magnetic resonance apparatus being located at a fixed point in the examination room. Even with variable-position magnetic resonance apparatuses, which can be moved for example by means of a suspended ceiling mount, a homogeneous magnetic field is merely given at the position at which the shimming method has been carried out. This represents a significant disadvantage for magnetic resonance apparatuses in which a position of the magnet in the examination room is able to be set as a function of a region of a patient's body and/or of an imaging examination to be carried out.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
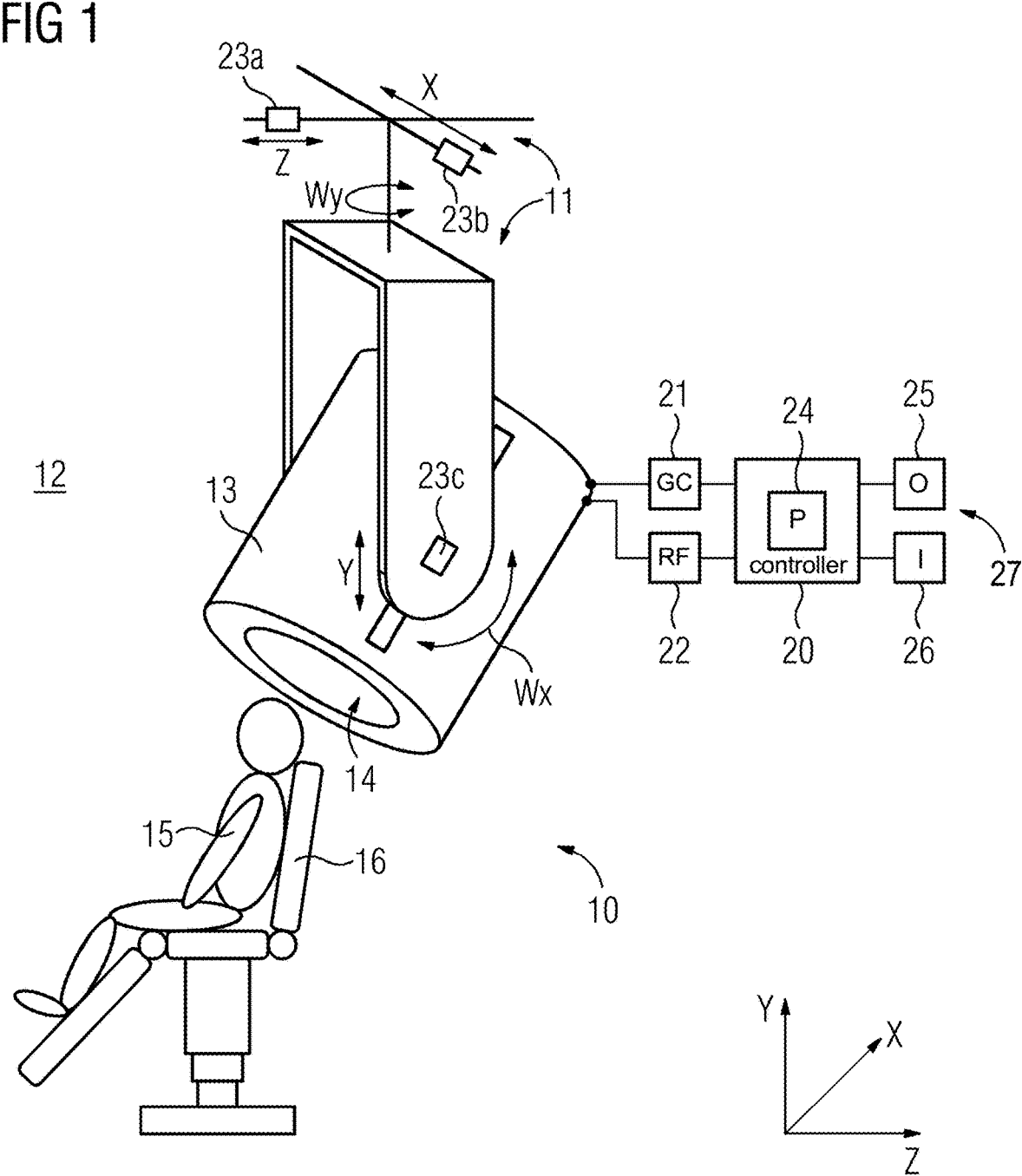
FIG. 1 shows a magnetic resonance apparatus according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to support an adjustment of a shim parameter of a shim element of a variable-position magnetic resonance apparatus.

In an exemplary embodiment, the magnetic resonance apparatus comprises at least one sensor.

The magnetic field of the magnetic resonance apparatus can in this case in particular represent a static main magnetic field (B0 magnetic field) of the magnetic resonance apparatus, which is provided by a main magnet of the magnetic resonance apparatus.

The magnetic resonance apparatus is able to be positioned in an examination room. A positioning of the magnetic resonance apparatus can in particular comprise a change to a spatial location of the magnetic resonance apparatus relative to the examination room. In an exemplary embodiment, a spatial location of the magnetic resonance apparatus is characterized by a position, such as e.g. a plurality of coordinates in a coordinate system formed by the examination room, and/or by an orientation of the magnetic resonance apparatus in the examination room. It is further conceivable for the position of the magnetic resonance apparatus to be determined by a position of a center of gravity of the magnetic resonance apparatus or a magnet of the magnetic resonance apparatus. Furthermore, the position can also be characterized by an external contour, a patient imaging region and/or an isocenter of the magnetic resonance apparatus. In an exemplary embodiment, the spatial location moreover comprises information about an orientation of the magnetic resonance apparatus and/or of a magnet of the magnetic resonance apparatus. The orientation of the magnetic resonance apparatus and/or of the magnet can for example by characterized by a magnetic field direction of the magnetic field and/or by an alignment of the patient imaging region in relation to a flat reference surface of the examination room. The examination room can be any given room in which the magnetic resonance apparatus is set up and/or in which there can be an imaging examination of a patient by means of the magnetic resonance apparatus.

The at least one sensor of the magnetic resonance apparatus is embodied to determine a spatial location of the magnetic resonance apparatus in an examination room. The at least one sensor can have any given measurement principle, which is embodied to determine a position and/or an orientation of the magnetic resonance apparatus. Examples of suitable sensors are optical sensors, such as e.g. a 3D camera, an infrared camera, a 2D camera, a LASER distance sensor, but also non-optical sensors, such as e.g. an incremental encoder, an absolute encoder, an angle encoder, an ultrasound distance sensor, a Hall sensor, an inductive distance sensor, a capacitive distance sensor or the like. In an exemplary embodiment, the magnetic resonance apparatus has a plurality of sensors, which are embodied to determine the spatial location of the magnetic resonance apparatus in the examination room. A controller of a motor is also to be understood as one of the at least one sensor, which can initiate a predetermined movement of the motor. For example, the magnetic resonance apparatus can have a stepping motor with a plurality of switches, which are switched consecutively by a controller in order to create a rotation of the stepping motor. A number and/or a speed of switching processes of the plurality of switches can be employed here in order to determine a speed of rotation and/or a speed of advance of the stepping motor. It is likewise conceivable for the controller to represent a measurement device for a current drawn by the motor. A movement created by the motor can be correlated for example with a current consumption per unit of time. In this case there can be a determination of the movement created by the motor as a function of the current consumption per unit of time.

External influences, such as e.g. a position and/or a nature of construction materials of a building of the examination room and also of plant and/or machinery that is located in a vicinity of the magnetic resonance apparatus, can act in an undesired way on a homogeneity of the magnetic field of the magnetic resonance apparatus. Through the provision of an inventive magnetic resonance apparatus with the at least one sensor a spatial location of the magnetic resonance apparatus is able to be determined. By means of correlation of spatial locations of the magnetic resonance apparatus and the magnetic fields that are assigned to the spatial locations, external influences on the magnetic field are advantageously able to be quantified depending on their position. This enables an adjustment of a shim parameter of a shim element of the magnetic resonance apparatus to be supported in an advantageous manner Spatial locations of the magnetic resonance apparatus with undesired and/or increased interactions of the magnetic field with external components are able to be determined and avoided when carrying out an imaging examination.

In an exemplary embodiment the inventive magnetic resonance apparatus has a positioning apparatus, which is embodied to change the spatial location of the magnetic resonance apparatus.

In an exemplary embodiment, the positioning apparatus is configured to set a position and/or an orientation of the magnetic resonance apparatus and/or of the magnet of the magnetic resonance apparatus as a function of a position, an attitude and/or a region of a patient's body. The positioning apparatus can for example be embodied to set a height and/or an angle of inclination of the magnet of the magnetic resonance apparatus in the examination room in order to adjust the magnetic resonance apparatus from an examination of a knee region of a first patient to an examination of a head region of a second patient. It is conceivable for the positioning apparatus to have a rail system, a telescopic system and/or an articulated joint.

A change in the spatial location of the magnetic resonance apparatus can comprise a movement of the magnetic resonance apparatus with at least one degree of freedom, at least two degrees of freedom, at least three degrees of freedom or at least four degrees of freedom. The positioning apparatus can for example have a rail system, which is embodied to position the magnetic resonance apparatus along a first axis. The rail system can further be embodied to position the magnetic resonance apparatus along a second axis. The first axis and the second axis in this case can be arranged perpendicular to one another in one plane, which is essentially aligned orthogonally to a direction of a gravitational force. The magnetic resonance apparatus can further be able to be positioned along any given curved path, which lies in the plane of the first axis and the second axis. It is furthermore conceivable for the positioning apparatus to have a telescopic element or a further rail element, which is embodied to position the magnetic resonance apparatus along a third axis. The third axis can in this case be aligned perpendicular to the first axis and the second axis and/or essentially in parallel to the direction of the force of gravity. The magnetic resonance apparatus can thus be positioned along the first axis, the second axis and the third axis in a three-dimensional way in the examination room.

The positioning apparatus can further have an articulated joint and/or a hinge, which is embodied to set an orientation of the magnetic resonance apparatus. The setting of the orientation can in particular comprise a rolling, a pitching and/or a yawing of the magnetic resonance apparatus, i.e. a rotation of the magnetic resonance apparatus and/or of the magnet unit about the first axis, the second axis and/or the third axis. In an exemplary embodiment, the change in the spatial location of the magnetic resonance apparatus comprises a movement of the magnetic resonance apparatus with four degrees of freedom, five degrees of freedom or six degrees of freedom by means of the positioning apparatus.

By providing a positioning apparatus, the spatial location of the magnetic resonance apparatus can be adjusted to any given region of a patient's body. This enables an imaging examination of patients with a nervous or claustrophobic condition to be carried out in a sitting or standing position, whereby an improved cooperation of the patient during the imaging examination can be achieved.

In an exemplary embodiment of the inventive magnetic resonance apparatus the at least one sensor is an optical sensor, wherein the optical sensor is embodied to detect optical data, which comprises an indication of the spatial location of the magnetic resonance apparatus in the examination room.

An optical sensor can be embodied to determine the spatial location of the magnetic resonance apparatus in the examination room by utilizing a photoelectric effect. For example, the optical sensor can be embodied as a 3D camera, a 2D camera and/or an infrared camera, which is configured to detect image data from the magnetic resonance apparatus in the examination room. It is likewise conceivable for the optical sensor to be LASER distance sensor. The LASER distance sensor can for example be embodied to determine a distance to an external contour of the magnetic resonance apparatus or a wall of the examination room. In an exemplary embodiment, the magnetic resonance apparatus has a plurality of optical sensors, which can be mounted at a predetermined position of the magnetic resonance apparatus and/or of the examination room. It is furthermore conceivable for the plurality of optical sensors to be positioned at different positions of the magnetic resonance apparatus and/or the examination room in order to determine the spatial location of the magnetic resonance apparatus as a function of different measurement directions. The magnetic resonance apparatus can have a processor, which is embodied to process signals of the plurality of optical sensors. In an exemplary embodiment, the optical sensor or the plurality of optical sensors are further used for determining a position of a patient, for recognizing a patient movement and/or for determining a position of a local coil.

An optical sensor can advantageously be employed for recognizing a patient and/or a local coil and can thus expand a function of the magnetic resonance apparatus without demanding additional components. Further, by using optical sensors, an exact and reproducible determination of the spatial location of the magnetic resonance apparatus in the examination room can be provided.

In an exemplary embodiment of the inventive magnetic resonance apparatus the at least one sensor is embodied as a position encoder, wherein the position encoder is embodied to detect position data, which comprises an indication of a change of location and/or a change of angle of the magnetic resonance apparatus.

A position encoder can be embodied to output a signal that is proportional to a position of the position encoder along a measurement path. For example, the position encoder can be positioned on an actuating drive and/or a motor. The position encoder can be embodied in particular to determine a change of location and/or change of angle, such as e.g. a horizontal shift, a vertical shift, a tilt and/or turn, transmitted to the magnetic resonance apparatus and/or magnets. It is likewise conceivable for the position encoder to be positioned on a movement path of the magnetic resonance apparatus and to be embodied to determine a distance covered by the magnetic resonance apparatus and/or by the magnet. The position encoder can be embodied in this case as an incremental encoder or as an absolute encoder. For example, the position encoder can have a sliding contact, an optical sensing, a photoelectric sensing, a magnetic sensing, an interference sensing, an inductive sensing, a capacitive sensing, a toothed-wheel generator or the like. In an exemplary embodiment, the magnetic resonance apparatus has a plurality of position encoders, which are positioned for example on different actuating drives and/or different movement paths of the magnetic resonance apparatus and/or of the magnet. However, a position encoder can also be understood as a start position or an end position of a travel of a motor or of the magnetic resonance apparatus, which is detected by a motor of the magnetic resonance apparatus.

By means of a position encoder a low-cost solution for determining the spatial location of the magnetic resonance apparatus is advantageously able to be provided. Position encoders further allow expensive image processing methods, which are associated with optical sensors for example, to be avoided.

In an exemplary embodiment, the inventive magnetic resonance apparatus comprises at least one shim element, which is embodied to adjust a magnetic field of the magnetic resonance apparatus depending on a shim parameter, wherein the shim element is designed as:

A shim coil,
A shim plate, having a ferromagnetic material, and/or
A ferromagnetic fluid.

The at least one shim element can be embodied to enter into an interaction with a magnetic field of the magnetic resonance apparatus in order to change a property of the magnetic field, in particular a magnetic field strength and/or a magnetic field direction. The at least one shim element can in particular feature a material that manipulates or modifies the magnetic field. Examples of such materials are above all ferromagnetic substances, such as e.g. solids with portions of iron or ferromagnetic fluids. A shim parameter of a ferromagnetic shim element can for example represent a spatial position and/or orientation of the shim element.

A shim element can furthermore be embodied to create a magnetic field itself, which is superimposed on a magnetic field of the magnetic resonance apparatus. Such shim elements can in particular have a shim coil, such as e.g. a superconducting coil or a resistive coil. Shim coils usually have current flowing through them in order to generate a magnetic field. A shim parameter of a shim coil can for example be an electrical current that is flowing through the shim coil. In an exemplary embodiment, the magnetic resonance apparatus has a plurality of shim elements. A plurality of shim elements can comprise at least 5, at least 10, at least 20, at least 40 or at least 80 shim elements. It is furthermore conceivable for the magnetic resonance apparatus to have different shim elements, such as e.g. small shim plates based on iron, shim coils and/or shim elements with a ferromagnetic fluid.

A shim plate can have any given shape, such as e.g. a rod shape, a cube shape, an ovoid shape or a shape homomorphic thereto. In an exemplary embodiment, the shim plate consists of a ferromagnetic material, such as e.g. iron, cobalt, nickel as well as specific lanthanides, gadolinium and the like. It is however likewise conceivable for the shim plate to feature an alloy of a ferromagnetic material and a further, non-ferromagnetic filler.

In an exemplary embodiment, a ferromagnetic fluid has ferromagnetic nanoparticles, which are present as a fluid, in particular a solution, a suspension or an emulsion. In an exemplary embodiment, the magnetic resonance apparatus has a conveying device, which is embodied to relocate and/or to change a volume of the ferromagnetic fluid in the magnetic resonance apparatus in order to adjust a magnetic field of the magnetic resonance apparatus. A shim parameter of the ferromagnetic fluid can in particular comprise a fill level of the ferromagnetic fluid in a reservoir and/or an operating time of the conveying device. In an exemplary embodiment, the magnetic resonance apparatus has a plurality of shim plates and a plurality of shim coils.

In an exemplary embodiment, the magnetic resonance apparatus is embodied to compensate for a change in an external influence on the magnetic field of the magnetic resonance apparatus with a change of the spatial location by means of an adjustment of a shim parameter of the at least one shim element. For this a processor and/or a controller of the magnetic resonance apparatus can be configured to adjust a shim parameter of the at least one shim element depending on a magnetic field database in accordance with an exemplary embodiment described below.

By adjusting a shim parameter of a shim element an intrinsic inhomogeneity of the magnetic field and/or undesired influences on the magnetic field of the magnetic resonance apparatus can advantageously be compensated for. Through provision of a plurality of shim elements in particular higher-order inhomogeneities of the magnetic field can be compensated for. This advantageously enables a quality of magnetic resonance images of the magnetic resonance examination acquired to be improved. In particular, by means of a dynamic adjustment of a shim parameter of a shim element, inhomogeneities of the magnetic field of the magnetic resonance apparatus, which arise as a result of external influences when the spatial location of the magnetic resonance apparatus changes, can be compensated for.

The inventive method for supporting an adjustment of a shim parameter of a magnetic resonance apparatus has the following steps:

Determining a current spatial location of the magnetic resonance apparatus in the examination room by means of at least one sensor and Adjusting a shim parameter of at least one shim element of the magnetic resonance apparatus depending on the current spatial location of the magnetic resonance apparatus in the examination room and information from a magnetic field database, wherein the magnetic field database comprises information about a spatial location of the magnetic resonance apparatus as well as magnetic field data correlated with the spatial location.

A magnetic field database can comprise any given data structure that makes possible an organization, a linkage, a correlation and/or a storage of data and/or values. The data structure can be suitable in particular for an application of mathematical operations to the data and/or values. Examples of suitable data structures are tuples, arrays, vectors, matrices, tables, sets and the like. The magnetic field database at least comprises information about a spatial location of the magnetic resonance apparatus and information about the magnetic field of the magnetic resonance apparatus. In this case information about the spatial location of the magnetic resonance apparatus can in particular be linked to information about the magnetic field and/or assigned to the information about the magnetic field.

It is conceivable for the magnetic resonance apparatus and/or the magnet of the magnetic resonance apparatus for an imaging examination to be adjusted to a region of a patient's body. A spatial location of the magnetic resonance apparatus adjusted to the patient can accordingly represent a current spatial location of the magnetic resonance apparatus. It is however likewise conceivable for the current spatial location of the magnetic resonance apparatus also to be changed independently of an imaging examination, e.g. within the framework of maintenance, calibration, commissioning and suchlike. In an exemplary embodiment, the current location of the magnetic resonance apparatus in the examination is determined depending on a signal of the at least one sensor. In an exemplary embodiment, the at least one sensor is embodied in accordance with aspects of the inventive magnetic resonance apparatus described above.

The current spatial location of the magnetic resonance apparatus determined depending on the at least one sensor is in particular employed for an adjustment of the shim parameter of the at least one shim element. For example, the current spatial location of the magnetic resonance apparatus can essentially match a spatial location from the magnetic field database for which magnetic field data has already been determined in accordance with an exemplary embodiment described above. In this case the adjustment of the shim parameter of the at least one shim element can be undertaken depending on the magnetic field data already acquired for the spatial location. It is however likewise conceivable for the current spatial location of the magnetic resonance apparatus not to have a match for a spatial location from the magnetic field database. In this case a method for estimating, calculating, averaging, interpolation or the like can be applied in order to determine the magnetic field of the magnetic resonance apparatus at the current spatial location depending on magnetic field data already acquired of other spatial locations. A shim parameter and/or the at least one shim element can be designed for example in accordance with one of the exemplary embodiments of the inventive magnetic resonance apparatus described above.

By adjustment of the shim parameter depending on the magnetic field database and the current position of the magnetic resonance apparatus, a complex determination of the homogeneity of the magnetic field for a current spatial location of the magnetic resonance apparatus before an imaging examination can advantageously be avoided. Further, through the inventive method, a time-efficient setting of shim-parameters of at least one shim element can be made possible. It is thus conceivable for the adjustment of the shim parameter to be able to be carried out dynamically, i.e. even during a preparation for an imaging examination and/or during an imaging examination.

In accordance with an exemplary embodiment the inventive method further has the following steps:

Alignment of the magnetic resonance apparatus in a spatial location in the examination room, Acquisition of the magnetic field data of the magnetic field of the magnetic resonance apparatus for the aligned spatial location, Storage of information about the aligned spatial location of the magnetic resonance apparatus together with the acquired magnetic field data in the magnetic field database.

The alignment of the magnetic resonance apparatus in a spatial location in an examination room can in particular be done by means of a positioning apparatus in accordance with one of the exemplary embodiments of the inventive magnetic resonance apparatus described above. The positioning apparatus can be embodied to move the magnetic resonance apparatus along at least one first axis. In an exemplary embodiment, the magnetic resonance apparatus can be positioned by means of the positioning apparatus along a plurality of axes, for example two or three perpendicular axes. The perpendicular axes can be shifted in relation to one another so that a three-dimensional movement of the magnetic resonance apparatus in the examination room is made possible. It is furthermore conceivable for the magnetic resonance apparatus to be supported tiltably and/or rotatably with regard to at least one axis in order to adjust an orientation of the magnetic resonance apparatus to a patient and/or an imaging examination. The alignment of the spatial location of the magnetic resonance apparatus can be done in this case manually by a user, semi-automatically by means of a remote control or fully automatically. The alignment of the spatial location of the magnetic resonance apparatus can in particular comprise a setting of a position and/or an orientation of the magnetic resonance apparatus and/or of a magnet of the magnetic resonance apparatus.

The magnetic field data of the magnetic field of the magnetic resonance apparatus for the aligned spatial location can for example be acquired by means of magnetometer. The magnetometer can in particular be introduced into an imaging region of the magnetic resonance apparatus in order to acquire magnetic field data from the area of the imaging region. It is furthermore conceivable for the magnetic field data to be acquired by a receiver of the magnetic resonance apparatus. For this a volume of a reference substance, such as e.g. water or oil, can be introduced into the imaging region of the magnetic resonance apparatus and excited by means of a predetermined excitation pulse. A magnetic resonance signal of the reference substance received by means of the receiver can subsequently be analyzed in order to obtain information about the magnetic field strength and/or the magnetic field direction. The analysis of the received magnetic resonance signal of the reference substance can in particular comprise a comparison of an expected magnetic resonance signal of the reference substance with the received magnetic resonance signal.

In an exemplary embodiment, the information about the aligned spatial location of the magnetic resonance apparatus together with the acquired magnetic field data is stored in the magnetic field database, by means of a processor, on a memory unit of the magnetic resonance apparatus. The magnetic field database can however likewise be stored by means of a Cloud computer and/or on a memory unit of a Cloud. In an exemplary embodiment, the spatial location of the magnetic resonance apparatus and the magnetic field data are stored in the form of a data structure in accordance with an exemplary embodiment of the inventive method described above. The information about the spatial location in this case can in particular comprise position data. In an exemplary embodiment, such position data comprises a coordinate, an angle and/or a dimension, which describe a position and/or an orientation of the magnetic resonance apparatus.

The provision of a magnetic field database allows inhomogeneities of a magnet of the magnetic resonance apparatus, but also external influences on the magnetic field, to be acquired or mapped in an advantageous way for a plurality of spatial locations of the magnetic resonance apparatus. A user of the magnetic resonance apparatus can further be informed with the aid of the magnetic field database about the existence of external influences on the magnetic field. In an advantageous way this allows spatial locations of the magnetic resonance apparatus with especially high external influences on the magnetic field to be avoided when carrying out an imaging examination.

In an exemplary embodiment of the inventive method the alignment of the magnetic resonance apparatus and the acquisition of the magnetic field data is repeated for a plurality of spatial locations of the magnetic resonance apparatus in the examination room.

In an exemplary embodiment, magnetic field data is recorded for each of the spatial locations of the plurality of spatial locations of the magnetic resonance apparatus. During the storage of the magnetic field database each spatial location of the plurality of spatial locations of the magnetic resonance apparatus is assigned correlated magnetic field data. It is conceivable for the acquisition of the magnetic field data to be carried out for a plurality of at least two, at least three, at least four or at least five spatial locations of the magnetic resonance apparatus. It is however likewise conceivable for a number of spatial locations for which magnetic field data is acquired to be greater than five or greater than ten.

The acquisition of the magnetic field data for a plurality of spatial locations of the magnetic resonance apparatus allows external influences on the magnetic field of the magnetic resonance apparatus to be characterized with a desired spatial resolution. This enables inhomogeneities of the magnetic field at predetermined measurement positions of the magnetic resonance apparatus to be determined in an advantageous way in advance and to be considered in an adjustment of shim parameters.

In accordance with an exemplary embodiment of the inventive method the alignment of the magnetic resonance apparatus is done depending on a predetermined grid, wherein the predetermined grid has a plurality of points, which define permissible spatial locations of the magnetic resonance apparatus within the examination room.

In an exemplary embodiment, predetermined grid is adapted to the examination room. This can mean that the predetermined grid discretizes a volume of the examination room in an equidistant way or a non-equidistant way. For example, the predetermined grid has a number of volumes distributed evenly over the examination room, which can be occupied by the magnetic resonance apparatus. It is likewise conceivable for the predetermined grid to have a plurality of points distributed in the examination room at which the isocenter of the magnetic resonance apparatus can be positioned by means of the positioning apparatus. In an exemplary embodiment, the predetermined grid considers a geometry of the examination room and/or an already occupied volume of the examination room. This can mean that only those spatial locations of the magnetic resonance apparatus are considered by the predetermined grid that allow a positioning of the magnetic resonance apparatus without colliding with the examination room and/or an object in the examination room. Such spatial locations can also be considered as allowed spatial locations of the magnetic resonance apparatus.

The use of a predetermined grid allows a ratio of a coverage of the examination room to a number of spatial locations of the magnetic resonance apparatus to be maximized in an advantageous way. This allows external influences on the magnetic field of the magnetic resonance apparatus to be characterized in an especially efficient way for all allowed spatial locations of the magnetic resonance apparatus in the examination room.

In an exemplary embodiment, the inventive method further has the following steps:

Determination (S7) of at least one further spatial location of the magnetic resonance apparatus depending on an analysis of a homogeneity of a magnetic field at at least one spatial location depending on the magnetic field database and carrying out of the steps S1, S2 and S3 for the at least one further spatial location.

The homogeneity can be analyzed based on an algorithm or a function by means of a processor. In an exemplary embodiment, the homogeneity of the magnetic field is analyzed depending on a comparison of a plurality of measured values of the magnetic field strength and/or a plurality of measured values of the magnetic field direction of the magnetic field, which are acquired together with the magnetic field data for the at least one spatial location of the magnetic resonance apparatus. A plurality of measured values of the magnetic field strength can have at least one first measured value of the magnetic field strength and a second measured value of the magnetic field strength. Accordingly, the plurality of measured values of the magnetic field direction can comprise at least one first measured value of the magnetic field direction and a second measured value of the magnetic field direction. In an exemplary embodiment, the first measured value and the second measured value of the magnetic field strength and/or the magnetic field direction can be acquired at different positions within an imaging region of the magnetic resonance apparatus. It is further conceivable for the first measured value and the second measured value to be acquired essentially at the same time, within the framework of an individual measurement and/or at a constant spatial location of the magnetic resonance apparatus. A homogeneity of the magnetic field can in particular be characterized by a spatial distribution of a plurality of measured values of the magnetic field directions, such as e.g. the first measured value of the magnetic field direction, the second measured value of the magnetic field direction, but also further measured values of the magnetic field direction. The homogeneity of the magnetic field can thus be understood as a spatial distribution of the magnetic field direction of the magnetic field. The homogeneity can in this case comprise the spatial distribution of the magnetic field direction of the magnetic field of the at least one spatial location. It is however likewise conceivable for the homogeneity also to take account of a spatial distribution of the magnetic field direction of one or more neighboring spatial locations.

It is conceivable that, in the analysis of the homogeneity of the magnetic field, a region with an irregularity is determined, wherein a distribution density of the plurality of spatial locations of the magnetic resonance apparatus for which magnetic field data is acquired is increased in a vicinity of the determined region with the irregularity. An irregularity can in particular identify a region in which a first measured value of the magnetic field strength and a second measured value of the magnetic field strength and/or a first measured value of the magnetic field direction and a second measured value of the magnetic field direction of the magnetic field deviate from one another by more than a predetermined degree. The irregularity can further be characterized by a deviation and/or a change of leading sign of a first measured value of the magnetic field direction by comparison with a second measured value of the magnetic field direction. For example, the irregularity can represent a local curvature and/or a local gradient of the magnetic field direction of the magnetic field. It is furthermore conceivable for the analysis of the homogeneity of the magnetic field to comprise a determination of a cause of the irregularity. For example, the homogeneity of the magnetic field can be characterized by means of a repeated acquisition of the magnetic field data at a plurality of spatial locations of the magnetic resonance apparatus in the examination room. In this case external influences on the homogeneity of the magnetic field of the magnetic resonance apparatus can be distinguished from an intrinsic inhomogeneity of the magnet.

Inhomogeneities of the magnet can essentially be independent of the spatial location of the magnetic resonance apparatus and can thus be distinguished from external influences. Through the determination of at least one further spatial location of the magnetic resonance apparatus and also the alignment of the magnetic resonance apparatus in the at least one further spatial location, the acquisition of magnetic field data of the magnetic field of the magnetic resonance apparatus at the at least one further spatial location and the storage of the information about the aligned spatial location of the magnetic resonance apparatus together with acquired magnetic field data in the magnetic field database, the predetermined grid or the plurality of points of the predetermined grid at those spatial locations of the magnetic resonance apparatus is able to be expanded and/or more highly resolved at which irregularities are analyzed.

By increasing a distribution density of acquired magnetic field data in an environment of the region with the irregularity determined, in particular local and/or position-dependent interactions of the magnetic field with external influences are able to be characterized. This enables the expanded magnetic field also to be determined for such regions in an advantageous way with a high accuracy.

In an exemplary embodiment of the inventive method the determination of the current spatial location of the magnetic resonance apparatus in the examination room comprises an acquisition of, using the at least one sensor:
  optical data, which contains an indication of the current spatial location of the magnetic resonance apparatus in the examination room and/or
  position data, which contains an indication of a change of location and/or a change of angle of the magnetic resonance apparatus.

The at least one sensor may be configured as an optical sensor and/or a position encoder in accordance with one or more embodiment of the inventive magnetic resonance apparatus described above. In an exemplary embodiment, the optical data and/or the position data of the at least one sensor are transmitted to a processor of the magnetic resonance apparatus. The processor can be embodied to process the optical data and/or the position data in order to determine the current spatial location of the magnetic resonance apparatus. In an example the at least one sensor is a 3D camera, which acquires image data of the magnetic resonance apparatus in the examination room and transmits it to the processor. The processor can in particular have an image processor, which processes the image data of the 3D camera and determines the current location of the magnetic resonance apparatus in the examination room depending on the image data. It is however likewise conceivable for the at least one sensor to have a 2D camera, an infrared camera, a plurality of 2D cameras, a plurality of 3D cameras and/or a plurality of position encoders.

A position encoder and/or an optical sensor are further able to be used for recognizing a position of the magnetic resonance apparatus, of the patient and/or of a local coil and also of further medical devices on the patient. The multiple use of the at least one sensor for different functions of the magnetic resonance apparatus enables a number of components to be minimized in an advantageous way and/or an outlay of a technical implementation of the inventive method to be reduced.

In an exemplary embodiment, the inventive method further has the following step:
  Determination of an expected magnetic field depending on the current spatial location of the magnetic resonance apparatus and information from the magnetic field database by means of a function, wherein the shim parameter of the at least one shim element is adjusted depending on the expected magnetic field.

In this exemplary embodiment, the current spatial location of the magnetic resonance apparatus can differ from a spatial location from the magnetic field database. The function here can have any given algorithm that determines the expected magnetic field of the current spatial location depending on a magnetic field of at least one nearest spatial location from the magnetic field database. It is furthermore conceivable for the function to determine the expected magnetic field depending on two, three or more spatial locations with corresponding magnetic field data from the magnetic field database. Averaging methods, interpolation methods, extrapolation methods, methods of a compensation calculation or the like can be used for this. The expected magnetic field can in particular represent an approximation, which approximates a magnetic field actually present at the current spatial location. In an exemplary embodiment, the information from the magnetic field database is characterized at least by measured values of a magnetic field of a spatial location.

The use of the function and the inventive magnetic field database allows an expected magnetic field of any given current location of the magnetic resonance apparatus to be approximated in an advantageous way. This enables an effort for an acquisition of magnetic field data of a plurality of spatial locations of the magnetic resonance apparatus in the examination room to be reduced or minimized in an advantageous way.

In an exemplary embodiment of the inventive method the determination of the expected magnetic field by means of the function comprises an application of at least one of the following methods:

An interpolation method,
An extrapolation method,
A compensation calculation,
A simulation method, and/or
A creation of an empirical model.

As described above, the function can have an algorithm that determines the expected magnetic field of the current spatial location depending on a magnetic field of at least one nearest spatial location and/or of a plurality of magnetic fields of a number of spatial locations. In the interpolation method and the extrapolation method magnetic field data from at least two known spatial locations from the magnetic field database can be employed to determine the expected magnetic field. In an exemplary embodiment, the at least two known spatial locations represent two nearest or neighboring spatial locations, which in a virtual space adjoin the current spatial location. A compensation calculation can in particular comprise a regression method, a fitting method and/or an optimization method. It is conceivable for a model and/or a model function, which describes inhomogeneities of the magnetic field of the magnetic resonance apparatus depending on a plurality of spatial locations of the magnetic resonance to be adjusted by means of the compensation calculation. Here in particular a least squares method can be employed to minimize a sum of a squared difference between magnetic field data of the magnetic field database and a result of the model and/or the model function. Furthermore, an empirical model and/or a simulation method can be employed in order to determine the expected magnetic field depending on the current spatial location of the magnetic resonance apparatus and information from the magnetic field database. In one example inhomogeneities of the magnetic field can be characterized and/or quantified depending on the magnetic field data of different spatial locations of the magnetic field database. Depending on the inhomogeneities of the magnetic field at different spatial locations, an empirical model and/or a simulation model can be created, which describes the external influence. The empirical model and/or the simulation model are subsequently able to be used for the determination of the expected magnetic field. As well as this, further methods, such as e.g. an analytical calculation and/or a numeric simulation of electromagnetic interactions of the magnetic field of the magnetic resonance apparatus with external influences, such as e.g. construction materials and/or devices in a vicinity of the examination room, are naturally conceivable.

The use of one or more of the methods described above for determining the expected magnetic field by means of the function enables the expected magnetic field to be determined in a robust and reproducible way. Furthermore, the expected magnetic field of any given current spatial location of the magnetic resonance apparatus is able in an advantageous way to be determined depending on a limited number of magnetic field data acquired by measurement and correlated with spatial locations.

In an exemplary embodiment of the inventive method the adjustment of the shim parameter of the at least one shim element comprises:

An adjustment of a spatial location of a shim plate,
An adjustment of an operating parameter of a shim coil and/or
A relocation of a ferromagnetic fluid and/or a change to a volume of the ferromagnetic fluid of the magnetic resonance apparatus.

The adjustment of the spatial location of a shim plate can in particular comprise a positioning and/or an orientation of the shim plate relative to the magnetic resonance apparatus. In an exemplary embodiment, by means of the shim plate, above all an inhomogeneity of the magnet of the magnetic resonance apparatus is compensated for. This can mean that the shim plates are connected mechanically once to the magnetic resonance apparatus in a predetermined position and/or orientation. It is however likewise conceivable for the position and/or orientation of the shim plate to be changed via actuating drives relative to a spatial location of the magnetic resonance apparatus.

An operating parameter of the shim coil can be adjusted as described above. In an exemplary embodiment, the adjustment of the operating parameter of the shim coil comprises at least an adjustment of a current through the shim coil. The shim coil in this case can be designed as a part of a gradient system of the magnetic resonance apparatus, in particular as a gradient coil. An adjustment of the operating parameter can for example comprise an adjustment of a current through the gradient coil, in order to compensate for a deviation from a desired homogeneity of the magnetic field through an external influence on the magnetic field in a current spatial location of the magnetic resonance apparatus. It is however likewise conceivable for the shim coil to be present separately from the gradient system. Such shim coils can be used in particular for a compensation for non-linear inhomogeneities and/or higher orders of inhomogeneities.

The relocation of ferromagnetic fluid in the magnetic resonance apparatus can in particular comprise a shifting of a predetermined volume of a ferromagnetic fluid from a first reservoir of the magnetic resonance apparatus into a second reservoir of the magnetic resonance apparatus. It is however likewise conceivable for the first reservoir or the second reservoir to be positioned outside the magnetic resonance apparatus. In a relocation of the ferromagnetic fluid between the first reservoir and the second reservoir a volume of the ferromagnetic fluid in the magnetic resonance apparatus can thus increase or decrease as required. The relocation of the ferromagnetic fluid can for example be done using a conveying device and/or a hydraulic facility, such as e.g. a pump, a valve, a non-return valve, a motorized valve and the like. An operating parameter in this case can in particular represent a fill level of the first reservoir and/or the second reservoirs, but also a rotational speed or a volume flow of the conveying device.

The adjustment of the aforementioned operating parameters of shim elements allow both inhomogeneities of the magnet and also inhomogeneities as a result of external influences on the magnetic field to be compensated for. Further, through the use of a plurality of different shim elements, dedicated operating parameters of those shim elements that make possible an especially efficient adjustment of the magnetic field can be adjusted in an advantageous way.

The inventive computer program product is able to be loaded into a memory unit of a processor of an inventive magnetic resonance apparatus in accordance with an exemplary embodiment described above, having program code means for carrying out an inventive method according to one of the exemplary embodiments described above, when the computer program product is executed in the processor of the magnetic resonance apparatus.

The inventive computer program product enables the inventive method to be carried out quickly, identically repeatably and robustly. The computer program product is configured so that is can carry out the inventive method steps by means of the processor. The processor in this case must have the preconditions, such as for example a corresponding main memory, a corresponding graphics card or a corresponding logic unit in each case, so that the respective method steps can be carried out efficiently. The computer program product is stored on a computer-readable medium for example or held on a network, a server or a Cloud, from where it can be loaded into the processor of a local processor. The processor can be embodied in this case as a self-contained system component or as a part of the magnetic resonance apparatus. Furthermore, control information of the computer program product can be stored on an electronically-readable data medium. The control information of the electronically-readable data medium can be embodied in such a way that, when the data medium is used in the processor of the magnetic resonance apparatus it carries out an inventive method. Examples of electronically-readable data media are a DVD, a magnetic tape, a USB stick or any other data medium on which electronically-readable control information, in particular software, is stored. When this control information is read from the data medium and transmitted to a controller and/or the processor of the magnetic resonance apparatus, all inventive embodiments of the inventive method described can be carried out.

FIG. 1 shows a schematic diagram of an inventive magnetic resonance apparatus 10, which is suitable for an imaging examination of a head region of patient 15. The inventive magnetic resonance apparatus 10 can however likewise be used for carrying out further imaging examinations, such as e.g.

A cardiac imaging,
A mammography imaging,
A neurological imaging,
A urological imaging,
An orthopedic imaging,
An ophthalmological imaging,
A prostate imaging,
and/or configured for any given imaging examination of other regions of the body of the patient 15.

For this purpose, the magnetic resonance apparatus 10 and/or a magnet unit 13 of the magnetic resonance apparatus 10 can be positioned by means of a positioning apparatus (positioner) 11 relative to an examination room 12 and/or a diagnostically relevant region of the body of the patient 15.

The magnetic resonance apparatus 10 comprises a magnet unit 13 and an imaging region 14 that is embodied to image an examination object 15, such as e.g. the head of the patient 15. The imaging region 14 in the present example is embodied in a cylindrical shape and is enclosed on its outer circumference by the magnet unit 13. The patient 15 can be positioned for an imaging examination on a patient support apparatus 16. It is conceivable for the magnet unit 13 to be able to be positioned by means of a positioning apparatus 11 in a spatial direction Z, a spatial direction X and/or a spatial direction Y in order to match the imaging region 14 to the diagnostically relevant region of the body of the patient 15. The positioning apparatus 11 can in particular have a rail system, a telescopic system and/or an articulated joint, which are embodied to set a position and/or an orientation of the magnetic resonance apparatus 10 and/or of the magnet unit 13 relative to the examination room 12 and/or the diagnostically relevant region of the body of the patient 15. For example, the articulated joint of the positioning apparatus 11 can be embodied to rotate the magnet unit 13 in a direction of rotation Wx, a direction of rotation Wy and/or a direction of rotation Wz. Further forms of embodiment of the positioning apparatus 11 are naturally conceivable (see e.g. FIGS. 2 and 3).

The magnet unit 13 has at least one magnet (not shown), which is embodied to create a magnetic field in the imaging region 14. The magnet can for example have a permanent magnet and/or an electromagnet based on a resistive coil, a superconductor and/or a high-temperature superconductor. The magnet unit 13 can in particular have a gradient coil (not shown) for creating magnetic gradient fields, which are used for a spatial encoding during imaging. The gradient coil is activated by means of a gradient controller 21 of the magnetic resonance apparatus 10. The magnet unit 13 can furthermore have a radio-frequency antenna (not shown), which is embodied to emit a radio-frequency excitation pulse into the imaging region 14. In an exemplary embodiment, the radio-frequency antenna is configured to excite nuclear spins that are located in the imaging region 14. For this the radio-frequency antenna is activated by a radio-frequency controller 22 of the magnetic resonance apparatus 10. The radio-frequency antenna can furthermore be embodied to receive magnetic resonance signals from the imaging region 14.

To control the magnet unit 13 with the gradient controller 21 and the radio-frequency antenna, the magnetic resonance apparatus 10 has a controller 20. For this, the controller 20 can be connected electrically to the gradient controller 21 and the radio-frequency controller 22 by means of a signal connection. In an exemplary embodiment, the controller 20 is configured to control an imaging sequence, such as e.g. a GRE (gradient echo) sequence, a TSE (turbo spin echo) sequence or a UTE (ultra-short echo time) sequence. What is more, the controller 20 can comprise a processor 24, which is configured for coordination of an acquisition and/or evaluation of magnetic resonance signals, which are acquired from the imaging region 14. The processor 24 of the magnetic resonance apparatus 10 can furthermore be configured to employ reconstruction methods in order to reconstruct magnetic resonance images with the aid of the magnetic resonance data. The processor 24 can further be configured to determine a spatial location of the magnetic resonance apparatus 10 and/or of the magnet unit 13 depending on a signal of a sensor 23. It is in particular conceivable for the processor 24 to be configured to process data of a magnetic field database, comprising at least information about a magnetic field and a spatial location of the magnetic resonance apparatus 10. In an exemplary embodiment, the controller 20 (and/or one or more components therein)

includes processing circuitry configured to perform one or more functions and/or operations of the controller 20, including controlling the MR imaging apparatus 10 (and/or one or more components therein), processing magnetic resonance signals, reconstructing magnetic resonance images, processing input from the user of the magnetic resonance imaging apparatus 10 and/or providing an output to the user. Additionally, the controller 20 may include one or more internal and/or external memories configured to store data, such as control data, computer code executable by the processor 24, image data, or other data as would be understood by one of ordinary skill in the arts.

Furthermore, the magnetic resonance apparatus 10 comprises a user interface 27, which has a signal connection to the controller 20. Control information, such as e g imaging parameters, but also reconstructed magnetic resonance images, can be displayed on an output 25, for example on at least one monitor, of the user interface 27 for a user of the magnetic resonance apparatus 10. Furthermore, the user interface 27 has an input 26, by means of which parameters of a magnetic resonance examination can be entered by a user.

The magnetic resonance apparatus 10 can further have a local receive antenna (not shown), which, in a position in which it is used, is positioned on the diagnostically relevant region of the body of the patient 15. The local receive antenna can be embodied to acquire magnetic resonance signals of the region of the body of the patient 15 and transmit them to the processor 24 of the controller 20. In an exemplary embodiment, the local receive antenna has an electrical connecting line, which provides a signal connection to the radio-frequency controller 21 and the controller 20. Just like the radio-frequency antenna, the local receive antenna can also be embodied to excite nuclear spins and to receive magnetic resonance signals. For this the local receive antenna can be activated by the radio-frequency controller 21. In one example the local receive antenna is embodied as a head coil, which at least partly encloses a head of the patient 15.

In the present example the magnetic resonance apparatus 10 further has position encoders 23*a*, 23*b* and 23*c* (23*a-c*), which are embodied to determine a movement of the magnetic resonance apparatus 10 and/or the magnet unit 13 along a movement path. For this the position encoders 23*a-c* can in particular be connected to an actuating drive of the positioning apparatus 11. The movement path can for example represent a predetermined transport direction of the actuating drive and/or a movement along a guide of the rail system and/or of the telescopic system. In an exemplary embodiment, a position encoder 23 is embodied as a toothed wheel generator, which is embodied to determine a deflection as a result of a movement of a toothed wheel drive of positioning apparatus 11. A position encoder 23 can however likewise be embodied as an inductive position encoder or a Hall sensor, which determines a distance to a magnetic distance element along the movement path of the magnetic resonance apparatus 10.

In an exemplary embodiment, the position encoders 23*a-c* are embodied to transfer a signal that contains an indication of a change of position and/or a change of angle of the magnetic resonance apparatus 10, by means of a wireless or a wired signal connection to the processor 24. The processor 24 can be embodied to determine a current spatial location of the magnetic resonance apparatus 10 and/or of the magnet unit 13 depending on the signal of the position encoders 23*a-c*.

Figure 4:
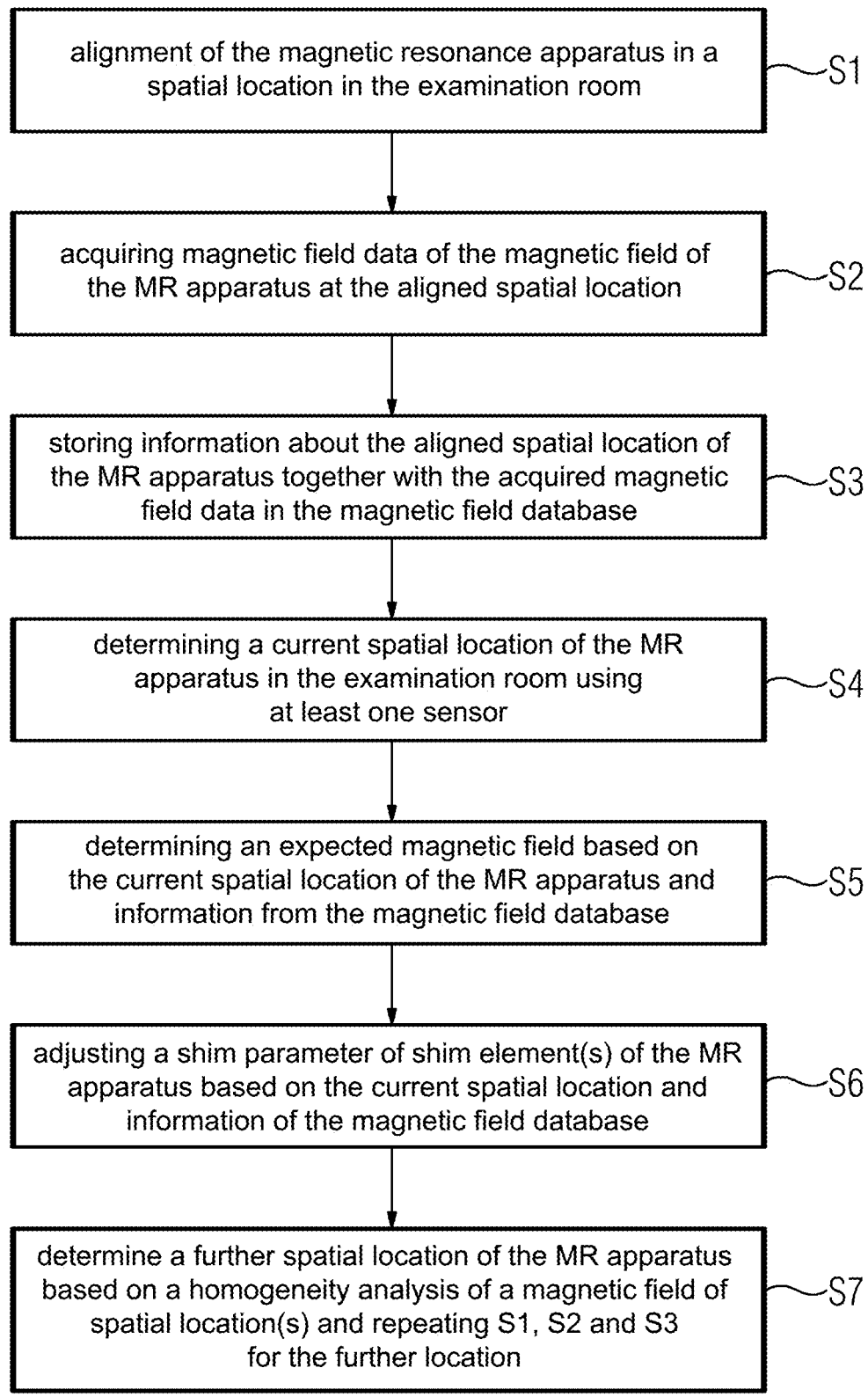
FIG. 4 shows a schematic flowchart of a method according to an exemplary embodiment.

In the example shown in FIG. 4 the shim elements can be designed as shim coils for example, which are positioned on the magnet unit 13 and/or at least partly enclose said unit (not shown). It is likewise conceivable for the magnetic resonance apparatus 10 to have inserts or holder elements on which shim plates can be installed and/or adjusted. Such inserts or holder elements can in particular be positioned on an inner side of the cylindrical magnet unit 13 (not shown). The magnet unit 13 can further comprise one or more reservoirs for a ferromagnetic fluid. Such reservoirs can be connected to one another and to a suitable conveying device by a fluid line system, in order to relocate the ferromagnetic fluid within the magnet unit 13 and/or between the magnet unit 13 and a reservoir in the environment. Inhomogeneities of a magnetic field created by the magnet unit 13 or also inhomogeneities caused by external influences can be adjusted by means of the settings of shim parameters of the shim elements.

The magnetic resonance apparatus 10 shown can of course also comprise further components that magnetic resonance apparatuses usually have. It is likewise conceivable for the magnetic resonance apparatus 10, instead of a cylindrical structure, to have a C-shaped, a triangular (e.g. an angled) or an asymmetrical structure of the magnet unit 13. The magnetic resonance apparatus 10 can in particular be embodied to carry out a magnetic resonance examination of a standing or sitting patient 15.

Figure 2:
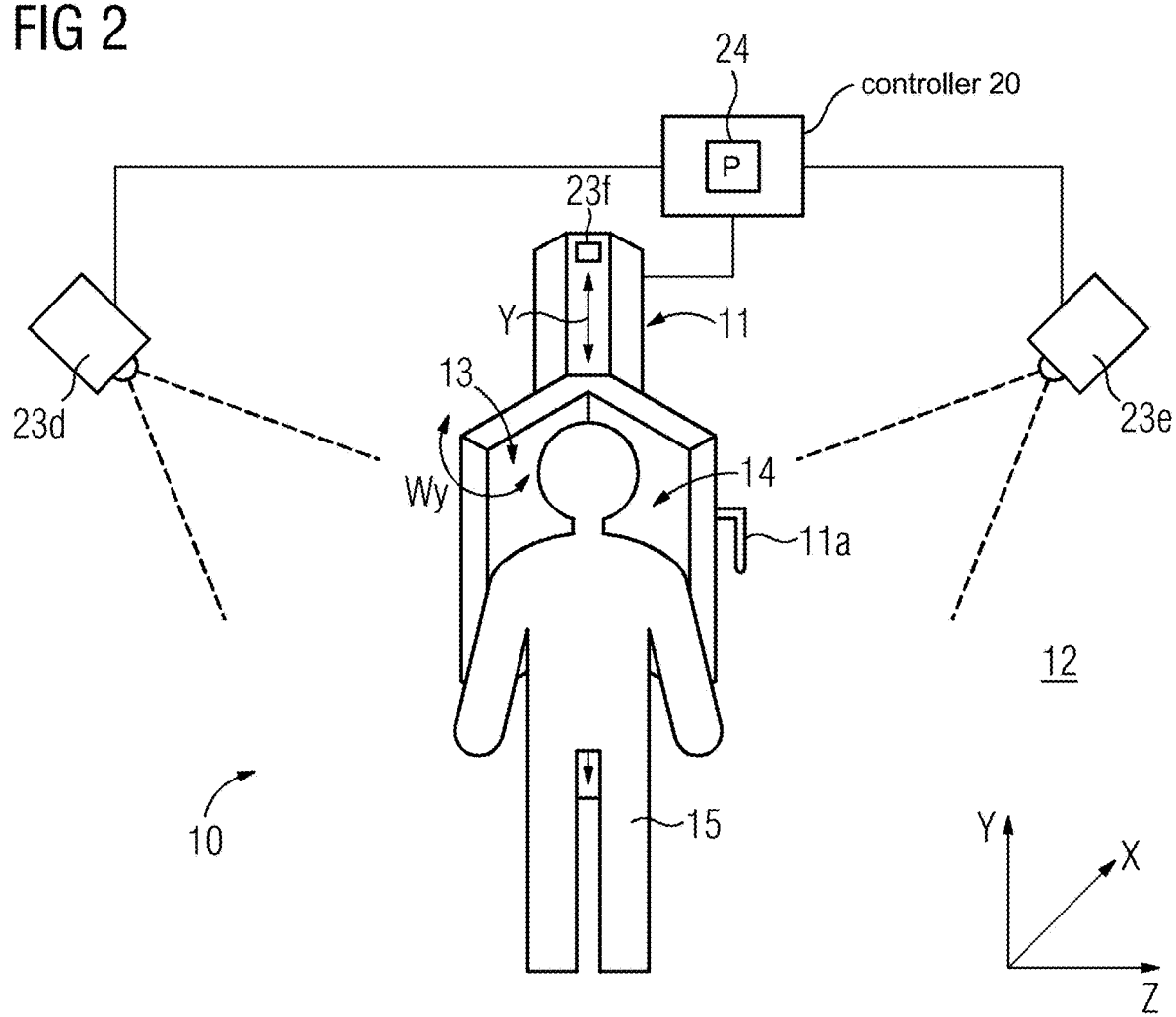
FIG. 2 shows a magnetic resonance apparatus according to an exemplary embodiment.

FIG. 2 shows an exemplary embodiment of the inventive magnetic resonance apparatus 10. In this example the magnetic resonance apparatus 10 has a magnet unit 13 in an angled arrangement. In an exemplary embodiment, the imaging region 14 is positioned at a distance from an outer contour of the magnetic resonance apparatus 10 in an angle of the magnet unit 13. An opening of the angled arrangement can in this case represent an access to the imaging region 14 of the magnetic resonance apparatus 10. The positioning apparatus 11 here is designed as a rail system, which is embodied to move the magnet unit 13 in the spatial direction Y. It is further conceivable for the positioning apparatus 11 to have at least one articulated joint, which makes it possible to change the orientation of the magnet unit 13 in the direction of rotation Wy. In the example shown, the positioning apparatus 11 further has a hand piece 11*a*, which is embodied to change a spatial location of the magnet unit 13 manually. The positioning apparatus 11 can however also have a drive of course, which is embodied to position the magnet unit 13 fully automatically or under remote control in at least one spatial direction.

The magnetic resonance apparatus 10 further has a position encoder 23*f* and also two 2D cameras 23*d* and 23*e*, which are embodied to acquire optical data of the magnetic resonance apparatus 10 in the examination room 12. The optical data can in particular comprise image data, which contains an indication of the current spatial location of the magnetic resonance apparatus 10 in the examination room 12. In an exemplary embodiment, the optical data is transmitted wirelessly or by wire to the processor 24. The processor 24 can in particular have an image processor, which is embodied to determine the current location of the magnetic resonance apparatus 10 depending on the optical data. The processor 24 can further be embodied to correlate position data of the position encoder 23*f* and also optical data of the 2D cameras 23*d* and 23*e*, in order to determine the current location of the magnetic resonance apparatus 10 and/or of the magnet unit 13. In this case of course the processor 24 is not restricted to using the sensors shown in FIG. 2. The magnetic resonance apparatus 10 can likewise have a number of sensors other than that shown in FIG. 1 and FIG. 2 with any given measurement principles.

Figure 3:
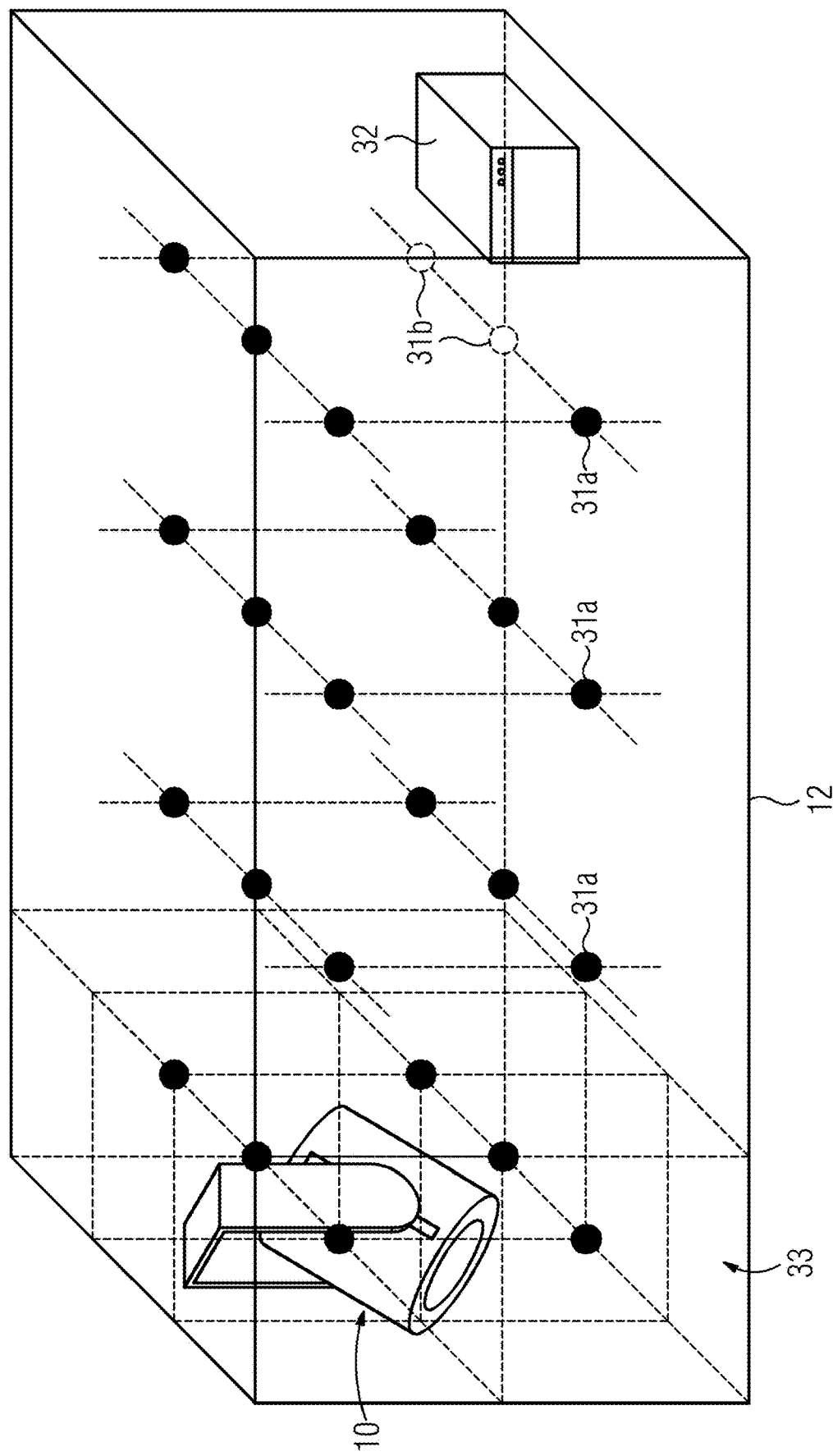
FIG. 3 shows a schematic representation of a predetermined grid in an examination room, according to an exemplary embodiment.

FIG. 3 shows an examination room 12 with an inventive magnetic resonance apparatus 10. In the present example the examination room 12 is divided up in accordance with the disclosure into a predetermined grid with a plurality of points 31, which discretize the examination room 12 in an equidistant way. It is conceivable for the plurality of points 31 to comprise allowed positions 31a and non-allowed positions 31b of the magnetic resonance apparatus 10 in the examination room 12. The plurality of points 31 in this case can already take account of movement radius of the magnetic resonance apparatus 10 and/or of the magnet unit 13, which is essentially achieved by an adjustment of the orientation of the magnetic resonance apparatus 10 and/or the magnet unit 13 by means of the positioning apparatus 11, in particular an articulated joint of the positioning apparatus 11. Such a movement radius is able to be considered for example by means of a square or cubic section 33 of the examination room 12. In the example shown a device 32 is located in the examination room 12, which can collide with the magnetic resonance apparatus 10 during a positioning of the magnetic resonance apparatus 10 at the non-allowed position 31b.

As well as the example shown, the examination room 12 can of course also be discretized in an uneven or random way. It is furthermore conceivable for the magnetic resonance apparatus 10 and/or the magnet unit 13 to have only a restricted number of movement paths, e.g. one, two or three movement paths, along which a corresponding discretization can be undertaken. The position and/or orientation of the magnetic resonance apparatus 10 show in FIG. 3 can represent a possible spatial location of the magnetic resonance apparatus 10 in the examination room.

FIG. 4 shows a possible flow diagram of an inventive method for supporting an adjustment of a shim parameter of a magnetic resonance apparatus 10.

In an optional step S1, there is an alignment of the magnetic resonance apparatus 10 in a spatial location in the examination room 12. Here the magnetic resonance apparatus 10 can be moved as shown in FIG. 1 and FIG. 2 by means of the positioning apparatus 11 relative to the patient 15 and/or the examination room 12. The alignment of the magnetic resonance apparatus 10 in this case can be done by hand by means of a hand piece 11a or under remote control or automatically by means of the positioning apparatus 11.

In an exemplary embodiment, the alignment of the magnetic resonance apparatus 10 and the acquisition of the magnetic field data for a plurality of spatial locations of the magnetic resonance apparatus 10 in the examination room 12 are repeated. In an exemplary embodiment, for each spatial location of the magnetic resonance apparatus 10 precisely one set of magnetic field data is recorded. A set of magnetic field data in this case can have a plurality of measured values of a magnetic field strength and/or a plurality of measured values of a magnetic field direction. The plurality of spatial locations of the magnetic resonance apparatus 10 can be distributed in any given way in the examination room 12 in this case.

In an exemplary embodiment, the alignment of the magnetic resonance apparatus 10 is done depending on a predetermined grid, wherein the predetermined grid has a plurality of points 31, which define allowed spatial locations of the magnetic resonance apparatus 10 within the examination room 12. The plurality of points 31 in this case, as shown in FIG. 3, can be distributed in an equidistant way in the examination room 12. In an exemplary embodiment, individual points 31 of the predetermined grid are selected so that a movement radius of the magnetic resonance apparatus 10 is considered. For this the examination room 12 can also be divided into sections 33, which take account of the movement radius of the magnetic resonance apparatus 10. In an exemplary embodiment a point 31 represents a center point of an isocenter of the magnetic resonance apparatus 10. In a further example the plurality of points 31 can also be distributed unevenly in the examination room 12 and/or only be positioned on predetermined movement paths of the magnetic resonance apparatus 10.

In an optional step S2, magnetic field data of the magnetic field of the magnetic resonance apparatus 10 is acquired at the aligned spatial location.

The acquisition of magnetic field data of the magnetic field of the magnetic resonance apparatus 10 in the aligned spatial location can for example be done by means of a magnetometer. The magnetometer is introduced here into an imaging region 14 of the magnetic resonance apparatus 10 in order to acquire magnetic field data from an area of the imaging region 14. In an exemplary embodiment, the magnetometer is aligned in this case at a plurality of positions in the imaging region 14 in order to acquire spatially-resolved values of the magnetic field strength and/or the magnetic field direction. It is furthermore conceivable for the magnetic field data to be acquired by a receiver, such as e.g. the radio-frequency antenna and/or the local receive antenna, of the magnetic resonance apparatus 10. For this a volume of a reference substance, such as e.g. water or oil, can be introduced into the imaging region 14 of the magnetic resonance apparatus 10 and excited by means of a predetermined excitation pulse. It is in particular conceivable for a phantom with a plurality of volumes with reference substances to be positioned in the imaging region 14. The phantom and/or the volumes with the reference substances can be positioned in this case so that spatially-resolved magnetic field data of an imaging volume, in particular an isocenter, of the magnetic resonance apparatus 10 can be acquired. A magnetic resonance signal of the reference substance received by means of the receiver can subsequently be analyzed in order to obtain the information about the magnetic field strength and/or the magnetic field direction.

In accordance with an optional step S3, information about the aligned spatial location of the magnetic resonance apparatus 10 is stored together with the acquired magnetic field data in the magnetic field database. In an exemplary embodiment, the storage of the spatial location with the correlated magnetic field data comprises storage as a tuple, an array, a vector, a matrix, a table, a set or the like. Thus, an organization, a linkage, a correlation and/or a use of mathematical operations on the data and/or values of the magnetic field database can be simplified.

In a step S4, there is a determination of a current spatial location of the magnetic resonance apparatus 10 in the examination room 12 by means of the at least one sensor 23. In an exemplary embodiment, the determination of the current spatial location of the magnetic resonance apparatus 10 comprises an acquisition of a signal from the at least one sensor 23 by means of an interface 27 of the magnetic resonance apparatus 10. The signal of the at least one sensor 23 can be transferred in particular to the processor 24, which determines the spatial location of the magnetic resonance apparatus 10 in the examination room 12 depending on the signal.

In an exemplary embodiment, the determination of the current spatial location of the magnetic resonance apparatus 10 in the examination room 12 comprises:
- An acquisition of optical data, which contains an indication of the current spatial location of the magnetic resonance apparatus 10 in the examination room 12, and/or
- An acquisition of position data, which contains an indication of a change of location and/or a change of angle of the magnetic resonance apparatus 10, The acquisition(s) can use the at least one sensor 23. The at least one sensor 23 here can in particular be embodied as a position encoder and/or a camera. The processor 24 processes the acquired optical data and/or position data of the at least one sensor 23 in order to determine the spatial location of the magnetic resonance apparatus 10 in the examination room 12.

In an optional step S5, an expected magnetic field is determined by means of a function, depending on the current spatial location of the magnetic resonance apparatus 10 and information from the magnetic field database. In one example the current spatial location essentially matches a spatial location of the magnetic resonance apparatus 10 from the magnetic field database. Thus, a magnetic field, which is correlated with this spatial location of the magnetic field database, can be accepted as the magnetic field of the current spatial location. It is conceivable in particular for the magnetic field database to comprise a plurality of spatial locations of the magnetic resonance apparatus 10 in the examination room 12, which are frequently set for different imaging examinations as current spatial locations. The function determines in this example a magnetic field of a spatial location of the magnetic field database, which matches the current spatial location of the magnetic resonance apparatus 10. The magnetic field determined can subsequently be accepted and/or set as the expected magnetic field.

In an exemplary embodiment, the determination of the expected magnetic field by means of the function comprises an application of at least one of the following methods:
- An interpolation method,
- An extrapolation method,
- A compensation calculation,
- A simulation method, and/or
- A creation of an empirical model.

In this embodiment, there is no match between the current spatial location of the magnetic resonance apparatus 10 and a spatial location in the magnetic field database. In a simple example the expected magnetic field of the current spatial location is determined by interpolation or extrapolation depending on magnetic field data of at least two nearest spatial locations from the magnetic field database by means of the function. It is however likewise conceivable for the function to comprise an application of a compensation calculation, a simulation method and/or a model-based method in order to determine the expected magnetic field at the current spatial location of the magnetic resonance apparatus 10.

In accordance with a further step S6, a shim parameter of at least one shim element of the magnetic resonance apparatus 10 is adjusted depending on the current spatial location of the magnetic resonance apparatus 10 in the examination room 12 and information of the magnetic field database. An adjustment of a shim parameter can for example comprise an adjustment of a current through a shim coil, an adjustment of a position and/or orientation of a shim plate and/or a relocation of a ferromagnetic fluid in the magnetic resonance apparatus 10. The information in the magnetic field database can for example comprise measured values of a magnetic field strength and/or a magnetic field direction, which are correlated with a spatial location at which the magnetic field was measured. In a simple example the current spatial location of the magnetic resonance apparatus 10 matches a spatial location from the magnetic field database. The magnetic field correlated with this spatial location can thus be accepted for the current spatial location. In an exemplary embodiment, the shim parameter of the at least one shim element is adjusted depending on the magnetic field of the matching spatial location in order to compensate for inhomogeneities of the magnetic field at the current spatial location.

In an exemplary embodiment, the adjustment of the shim parameter of the at least one shim element is done depending on the expected magnetic field. The expected magnetic field can be determined here as described under step S5.

In an optional step S7, at least one further spatial location of the magnetic resonance apparatus 10 is determined depending on an analysis of a homogeneity of a magnetic field of at least one spatial location depending on the magnetic field database and the steps S1, S2 and S3 are carried out for the at least one further spatial location. In an exemplary embodiment, in the analysis of the homogeneity of the magnetic field, a region with an irregularity is determined and a distribution density of the plurality of spatial locations of the magnetic resonance apparatus 10, at which magnetic field data is acquired, is increased in an environment of the region of the irregularity determined. It is conceivable that, in the analysis of a magnetic field of a spatial location from the magnetic field database, an irregularity with regard to the homogeneity of the magnetic field is determined. Such an irregularity can for example be a gradient of a measured magnetic field strength and/or a magnetic field direction. The steps S1 to S3 of the inventive method can subsequently be repeated in an environment, especially in an immediate vicinity, of the spatial location with the magnetic field with the irregularity. Repeating the steps S1 to S3 enables the irregularity and/or an external influence that causes the irregularity to be characterized spatially-resolved. It is conceivable for an interpolation method and/or an extrapolation method for determining an expected magnetic field in a region with the irregularity to generate more precise results the more frequently the steps S1 to S3 are carried out in the region with the irregularity.

Exemplary embodiments of the inventive method and the inventive magnetic resonance apparatus described here can be understood as being by way of example. Individual embodiments are therefore able to be expanded by features of other embodiments. In particular the order of the method steps of the inventive method is to be understood as being by way of example. The individual steps can also be carried out in a different order or partly or completely overlap with one another in their timing.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A magnetic resonance apparatus, comprising:
   at least one shim element configured to adjust a magnetic field of the magnetic resonance apparatus based on a shim parameter;
   at least one sensor; and
   a controller configured to:
   position the magnetic resonance apparatus in an examination room;
   determine a current spatial location of the magnetic resonance apparatus in the examination room using the at least one sensor; and
   adjust the shim parameter of the at least one shim element based on the current spatial location of the magnetic resonance apparatus and information of a magnetic field database including information about a spatial location of the magnetic resonance apparatus and magnetic field data correlated with the spatial location.

2. The magnetic resonance apparatus as claimed in claim 1, further comprising a positioning apparatus, the controller being configured to control the positioning apparatus to change the spatial location of the magnetic resonance apparatus, wherein a change in the spatial location of the magnetic resonance apparatus comprises a movement of the magnetic resonance apparatus along at least one degree of freedom.

3. The magnetic resonance apparatus as claimed in claim 1, wherein the at least one sensor is an optical sensor configured to acquire optical data that comprises an indication of the current spatial location of the magnetic resonance apparatus in the examination room.

4. The magnetic resonance apparatus as claimed in claim 1, wherein the at least one sensor is a position encoder configured to acquire position data that comprises an indication of a change of position and/or a change of angle of the magnetic resonance apparatus.

5. The magnetic resonance apparatus as claimed in claim 1, wherein the at least one shim element is: a shim coil, a shim plate having a ferromagnetic material, and/or a ferromagnetic fluid.

6. A method for supporting an adjustment of a shim parameter of a magnetic resonance apparatus, the method comprising:
   determining, using at least one sensor, a current spatial location of the magnetic resonance apparatus in the examination room; and
   adjusting, by a controller, the shim parameter of at least one shim element of the magnetic resonance apparatus based on the current spatial location of the magnetic resonance apparatus in the examination room and information of a magnetic field database including information about a spatial location of the magnetic resonance apparatus and magnetic field data correlated with the spatial location.

7. The method as claimed in claim 6, further comprising:
controlling the magnetic resonance apparatus to align the magnetic resonance apparatus in a spatial location in the examination room,
acquiring magnetic field data of the magnetic field of the magnetic resonance apparatus in the aligned spatial location, and
storing information about the aligned spatial location of the magnetic resonance apparatus in the magnetic field database together with the acquired magnetic field data.

8. The method as claimed in claim 7, wherein the alignment of the magnetic resonance apparatus and the acquisition of the magnetic field data is repeated for a plurality of spatial locations of the magnetic resonance apparatus in the examination room.

9. The method as claimed in claim 8, wherein the alignment of the magnetic resonance apparatus is performed based on a predetermined grid having a plurality of points defining allowed spatial locations of the magnetic resonance apparatus within the examination room.

10. The method as claimed in claim 8, further comprising:
analyzing a homogeneity of a magnetic field of at least one spatial location based on the magnetic field database to determine the at least one further spatial location of the magnetic resonance apparatus based on the analysis; and
performing, for the at least one further spatial location:
alignment of the magnetic resonance apparatus in a spatial location in the examination room,
acquisition of magnetic field data of the magnetic field of the magnetic resonance apparatus in the aligned spatial location, and
storing of information about the aligned spatial location of the magnetic resonance apparatus in the magnetic field database together with the acquired magnetic field data.

11. The method as claimed in claim 6, wherein the determining of the current spatial location of the magnetic resonance apparatus in the examination room comprises:
acquiring, using at least one sensor, optical data indicative of the current spatial location of the magnetic resonance apparatus in the examination room; and/or
acquiring, using the at least one sensor, position data indicative of a change of location and/or a change of angle of the magnetic resonance apparatus.

12. The method as claimed in one of claim 6, further comprising:
determining an expected magnetic field based on the current spatial location of the magnetic resonance apparatus and information from the magnetic field database,
wherein the adjustment of the shim parameter of the at least one shim element is performed based on the expected magnetic field.

13. The method as claimed in claim 12, wherein the determination of the expected magnetic field comprises use of: an interpolation method, an extrapolation method, a compensation calculation, a simulation method, and/or creation of an empirical model.

14. The method as claimed in claim 6, wherein the adjustment of the shim parameter of the at least one shim element comprises:
an adjustment of a spatial location of a shim plate,
an adjustment of an operating parameter of a shim coil and/or
a relocation of a ferromagnetic fluid and/or a change to a volume of the ferromagnetic fluid of the magnetic resonance apparatus.

15. A non-transitory computer-readable storage medium with an executable program stored thereon, that when executed, instructs a processor to perform a method for supporting an adjustment of a shim parameter of a magnetic resonance apparatus, the method comprising:
determining, using at least one sensor, a current spatial location of the magnetic resonance apparatus in the examination room; and
adjusting the shim parameter of at least one shim element of the magnetic resonance apparatus based on the current spatial location of the magnetic resonance apparatus in the examination room and information of a magnetic field database including information about a spatial location of the magnetic resonance apparatus and magnetic field data correlated with the spatial location.

* * * * *